United States Patent [19]

Sarfarazi

[11] Patent Number: 5,275,623
[45] Date of Patent: Jan. 4, 1994

[54] ELLIPTICAL ACCOMMODATIVE INTRAOCULAR LENS FOR SMALL INCISION SURGERY

[76] Inventor: Faezeh Sarfarazi, 25 Wiswall Rd., Newton Center, Mass. 02159

[21] Appl. No.: 793,470

[22] Filed: Nov. 18, 1991

[51] Int. Cl.$^5$ .................................. A61F 2/16
[52] U.S. Cl. ........................................ 623/6
[58] Field of Search ............................... 623/6

[56] References Cited

U.S. PATENT DOCUMENTS

| | | | |
|---|---|---|---|
| 4,253,199 | 3/1981 | Banko | 623/6 |
| 4,466,705 | 8/1984 | Michelson | 623/6 |
| 4,685,922 | 8/1987 | Peyman | 623/6 |
| 4,764,169 | 8/1988 | Grendahl | 623/6 |
| 4,790,847 | 12/1988 | Woods | 623/6 |
| 4,842,601 | 6/1989 | Smith | 623/6 |
| 4,883,485 | 11/1989 | Patel | 623/6 |
| 4,932,966 | 6/1990 | Christie et al. | 623/6 |
| 4,946,469 | 8/1990 | Sarfarazi | 623/6 |

FOREIGN PATENT DOCUMENTS 0328117  8/1989  European Pat. Off. ............... 623/6

*Primary Examiner*—Randy C. Shay
*Attorney, Agent, or Firm*—Ellen C. Childress

[57] ABSTRACT

An elliptical accommodative intraocular lens assembly is provided for placement in the evacuated capsular bag of the posterior chamber of an eye after a small incision capsulorhexis, such that as the capsular bag is pulled and released by ciliary muscles, the lenses approach and withdraw from each other to provide focal accommodation.

33 Claims, 4 Drawing Sheets

ELLIPTICAL ACCOMMODATIVE INTRAOCULAR LENS FOR SMALL INCISION SURGERY

FIELD OF THE INVENTION

This invention relates to intraocular lenses for implanting in the capsular bag of the posterior chamber of the eye after an anterior capsulorhexis. After implantation the lens makes use of the ciliary muscle to adjust the refractive power of the lens.

BACKGROUND OF THE INVENTION

Cataract extraction is the most common ophthalmic surgical procedure performed in the United States. Extracapsular cataract extraction involves cutting a portion of the anterior capsule (anterior capsulorhexis) followed by removal of the nucleus. Alternatively, a probe may be inserted through the anterior capsule and ultrasonically vibrated, transforming lens material into an emulsion is then irrigated and aspirated from the capsular bag (phacoemulsification). After removal of the natural lens, images no longer focus on the retina and a replacement lens must be provided for clear vision. Replacement lenses can be glasses, contact lenses or intraocular lenses. Of these, intraocular lenses give the greatest convenience and undistorted vision, however, for insertion of a lens, the size of the incision is dictated by the size of the implant rather than requirements of removing the natural lens. Replacement lenses, however, lack the ability of a natural lens to accommodatively focus on near and far objects.

When a person looks at an object, light is reflected from the object through the cornea, the aqueous humor, through the pupil and into the lens which converges the light through the vitreous body onto the retina. To clearly focus on near objects, light rays must be bent more. To accomplish this the lens becomes more curved and thicker. Most of this change comes from pulling and relaxing the capsular bag at its equator. The equator of the bag is attached to the ciliary muscle by filaments called the zonules of Zinn which are in turn attached to the ciliary muscle. When looking at an object in the distance, the ciliary muscle relaxes and expands, thereby pulling on the zonules, flattening the capsule and lens. When looking at a near object, the ciliary muscle tenses and contracts moving the muscle sightly inward and relaxing the pull on the zonules, allowing the capsular bag to become more curved and thickened from front to back. The lens itself is composed of interlocking fibers which affect the elastic movement of the lens so that as the lens changes shape the fibers alter their curvature. As a person ages, the accommodative ability of the lens decreases which changes in the eye. Age related eye changes include thickening of the lens, an increase in the amount of insoluble protein in the lens, a migration in the points of attachment of the zonules away from the equator of the capsule, and partial liquefaction of the vitreous body.

Lenses are made from transparent material having the shape of a body of rotational symmetry, such as a sphere. The degree of curvature of the surface is inversely proportional to the radius of curvature and the focal length. Parallel light rays converge after being refracted through a convex surface and diverge after being refracted through a concave surface. Refractive power of a lens is dependent upon the refractive index of the lens material and the lens curvature. A simple lens has two sides, each with a curvature. Two lenses separated by a given distance, can be considered as one thick lens having two foci and two principal planes. The focal length of the system is the product of their focal lengths ($f_1$, $f_2$) divided by the sum of their focal lengths minus the distance (d) between them i.e.

$$F=(f_1 f_2)/(f_1 = f_2 - d)$$

When the space between the lenses is not a vacuum but contains a substance, the amount subtracted from the sum of the focal length is divided by the refractive index (n) of that substance.

$$F=(f_1 f_2)/(f_1 + f_2 - d/n)$$

The refractive power of a lens system is given by the inverse of the focal length. By using two fixed lenses and varying the distance between them, a system of variable focal length can be constructed. If the curvature of one or both of the lens surfaces increases as the distance between lenses is increased, and decreases as the distance between the lenses is decreased, the change in focal length is enhanced.

Several attempts have been made to provide the eye with focal length accommodation. The most familiar of these is a bi or multi-focal lens. These are used in glasses, contacts, and intraocular lenses but have a disadvantage in that the focal accommodation is dependent upon direction of focus.

U.S. Pat. No. 4,254,509 discloses a lens which takes advantage of the ciliary muscle. However, this lens is placed in the anterior chamber of the eye. Such implants are at times accompanied by complications such as damage to the vascular iris.

U.S. Pat. No. 4,253,199 discloses a lens attached directly to the ciliary body. The lens is in a more natural position but requires suturing to the ciliary body risking massive rupture during surgery and bleeding from the sutures.

U.S. Pat. No. 4,685,922, incorporated herein by reference, discloses a chambered lens system for which the refractive power can be changed. Such alteration is permanent, accomplished by rupture of the chambers.

U.S. Pat. No. 4,790,847 provides a single lens for in capsular bag implantation using rearwardly biased haptics which engage the capsular bag at its equator and move the lens forward and backward upon contraction and relaxation of the ciliary muscles.

U.S. Pat. No. 4,842,601, incorporated herein by reference, discloses a two section deformable lens assembly for implanting in the capsular bag. The lens allows division of refractive power and takes advantage of the action of the ciliary body and zonules on the capsular bag. This lens system is assembled after insertion.

U.S. Pat. No. 4,892,543 discloses another two lens assembly for placement in the posterior chamber, possibly in the bag where the capsular bag is not removed. This lens allows dividing the refractive power between two lenses and introduces a variable focal length in one of the lenses by compressing a flexible wall of one lens against the convex surface of the second fixed lens. This requires that the first and second lens be in substantially adjacent positions.

U.S. Pat. No. 4,932,966, incorporated herein by reference, presents an accommodative lens in which two lenses joined at their periphery enclosed a fluid filled sack, accommodation being accomplished selectively changing the fluid pressure in the sac. One lens is a rigid base lens and the other lens is membrane-like, the equatorial diameter of the lens assembly being substantially that of a dilated pupil and is supported by bladders or haptics.

BRIEF SUMMARY OF THE INVENTION

The present invention provides dual and thick lens optics, capable of accommodating focus at a range of distances in a simple unitary structure. It uses the eye capsule's natural shaping from the ciliary body to accommodate the focus. Embodiments provide for insertion into a small incision, natural centricity, and increased focusing of the components.

DESCRIPTION OF THE PREFERRED EMBODIMENTS

Figure 1:
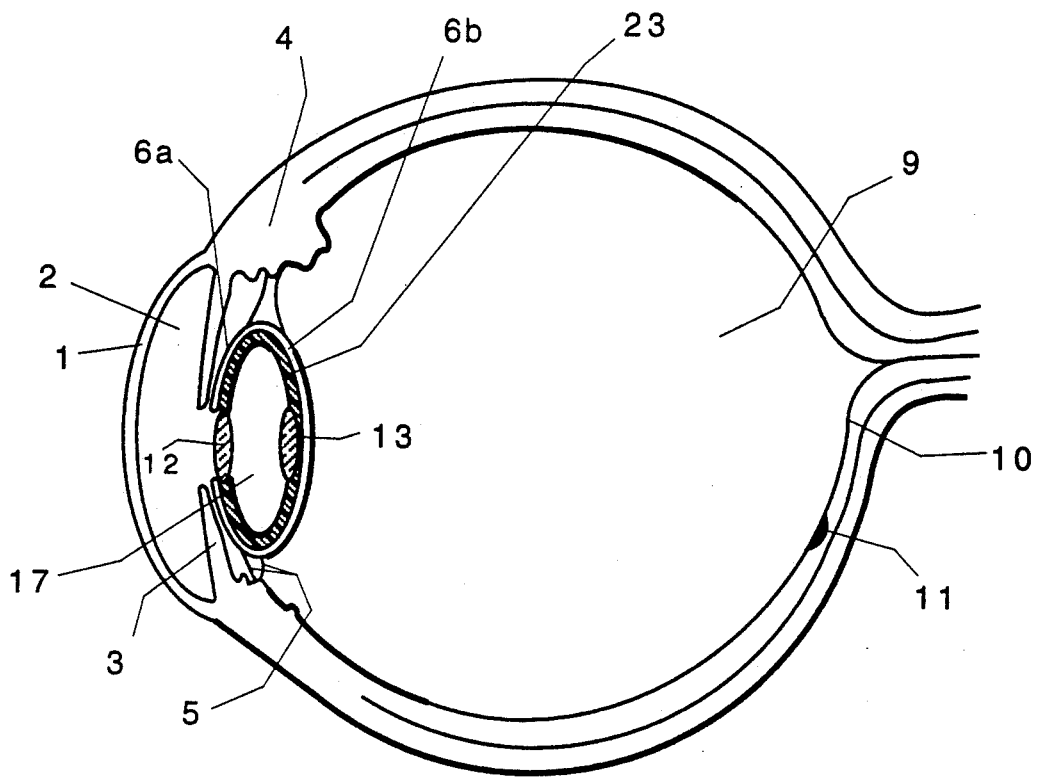
FIG. 1 is a cross sectional view of the eye with an accommodative lens of the invention in place.
Figure 2:
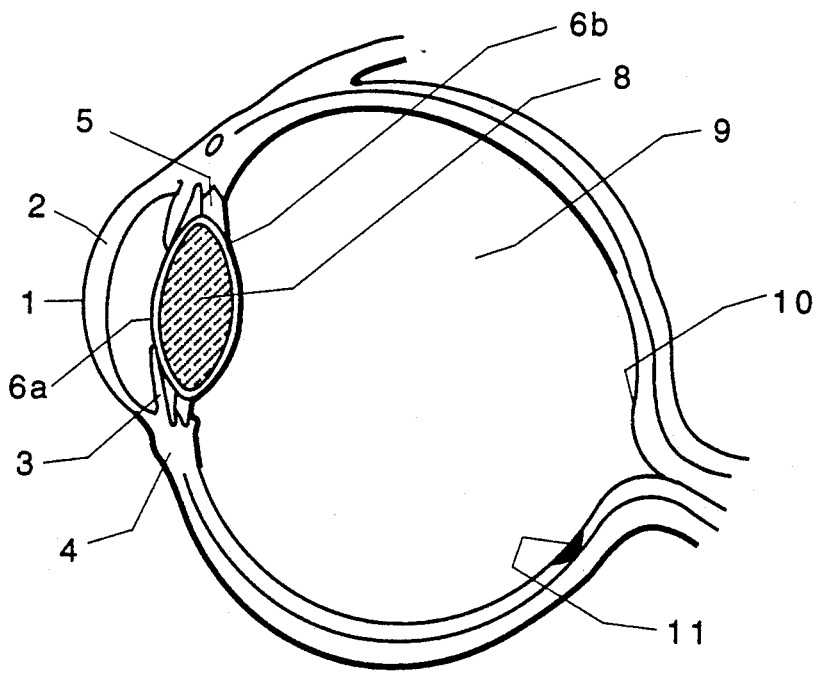
FIG. 2 is a vertical sectional view of an eye.

FIG. 2 shows a cross section of the eye. As light enters the eye it passes through the cornea 1; through the aqueous humor in the anterior chamber 2; through the pupil located centric of iris 3; through the anterior wall of the capsular bag 6a; is convergently refracted by the lens 8; passes through the posterior wall of capsular bag 6b; through the vitreous humor 9 to the retina 10 at the fovea 11. The shape of the lens capsule is controlled by ciliary muscle 4 attached to the capsule by filaments called zonules 5.

Figure 6:
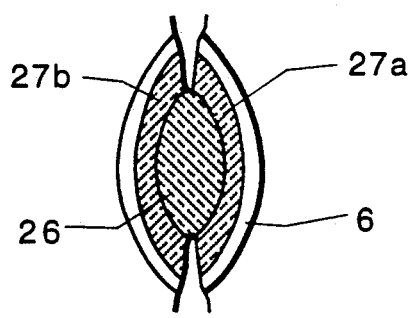
FIG. 6 is a schematic side view of the natural lens

The natural lens, shown in FIG. 6, has a central biconvex nuclear portion 26 surrounded by a concavo-convex menisci 27a and b. Lenses which are bi convex converge light rays. Lenses which are concavo-convex have a diverging effect on light rays. Therefore the menisci of the natural lens provides a moderating effect on the converging nucleus. The anterior-posterior or polar diameter of the lens is about 5 mm. The equatorial diameter is about 9 mm.

Figure 3:
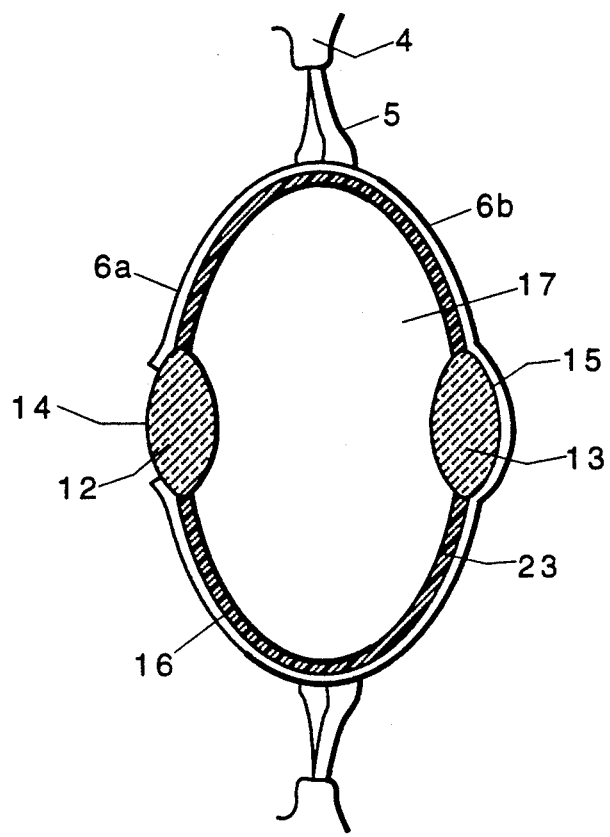
FIG. 3 is a partial sectional view showing an intraocular lens in accordance with the invention within the capsular bag when the eye is focused on a near object.
Figure 4:
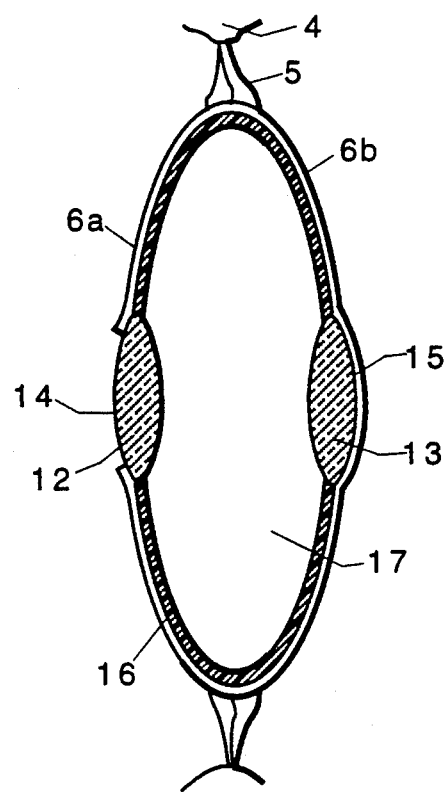
FIG. 4 is a partial sectional view showing the intraocular lens of FIG. 3 when the eye is focused on a distant object.

When the natural lens 8 is removed through capsulorhexis the intraocular implant shown in FIGS. 3 and 4 can restore focusing. The implant has an anterior lens 12 with an anterior surface 14 and a posterior lens 13 with an posterior surface 15. Extending from and connecting the equatorial perimeters of the anterior and posterior lenses is a flexible cell wall 16 forming a discoid cell 17 having an equatorial diameter substantially the same as the capsule 6. Cell 17 formed by the two lenses 12 and 13 is filled with a fluid (gas or liquid) such as air after implantation. Pressure around the equator of the cell supports the lens assembly in place.

Figure 8:
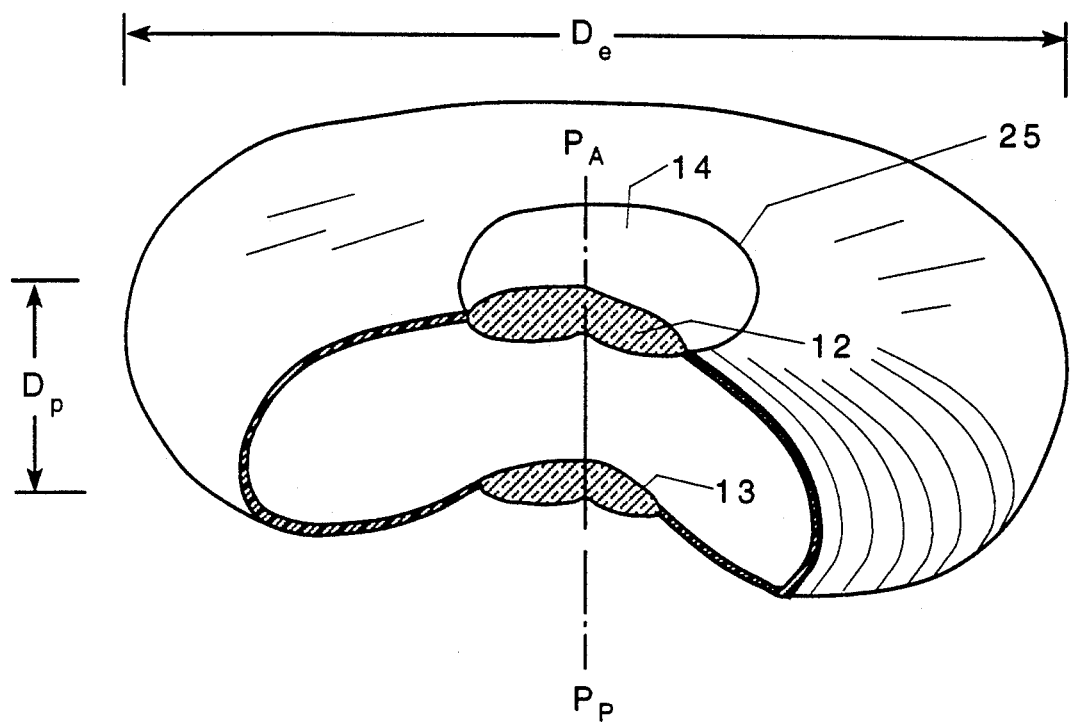
FIG. 8 is a perspective sectional view of the embodiment of FIG. 3.

FIG. 8 shows the same lens assembly having a cell equatorial diameter of $D_e$, a cell polar diameter of $D_p$, and a polar axis $P_aP_p$. The equatorial diameter 25 of the anterior lens 12 while ranging from 3-7 mm, here is substantially the size of a pupil (4-5 mm).

Figure 9:
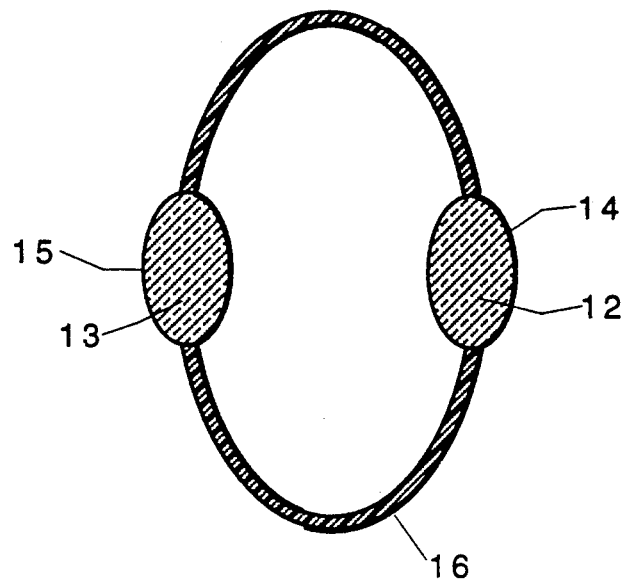
FIG. 9 is a cross sectional view of a lens assembly with optics having non-spherically convex surfaces.

The lens of FIG. 9 is an intraocular lens assembly with optics having non-spherically convex surfaces.

Although the lenses may be rigid or flexible, flexible lenses can provide greater accommodation. Anterior and posterior lenses, if rigid can be made out of a biocompatible, transparent material such as PMMA (polymethyl methacrylate), HEMA (hydroxyethyl methacrylate), polysulfones, polycarbonates, or a silicon polymer (polydimethyl siloxanes). Materials for a soft lens would include gel forming polymers such as silica hydrogels, polysaccharides such as hyaluronic acid, or a transparent, lens-shaped sack of polyvinyl alcohol. The equatorial diameter of the anterior lens is about the size of a dilated pupil or 5 mm. Posterior and anterior lenses have a thickness of 1 to 1.5 mm. For a typical eye the anterior radius of curvature for the anterior lens is between 8 and 14 mm., and the posterior radius of curvature for the posterior lens is between 4 and 7 mm. The curvature of both faces of each lens can be altered to correct for differences in the shape of the eye (i.e. myopia). Since both lenses are converging lenses with a space between them, focal length and power is divided between them, however, if desired, the power could be in one lens. The cell wall 16 has a thickness of 0.1 mm., and can be made of a methacrylate, silicon polymer or other biocompatible, flexible material such as olefin polymers. The discoid shape is preferably an ellipsoid having a polar diameter of about 5 mm. and an equatorial diameter of 9 mm. when filled. When the ciliary muscles 4 relax and swell, the zonules 5 pull on the equator of the capsule 6, the lens assembly flattens increasing its equatorial diameter and decreasing its polar diameter thus decreasing the distance between the two lenses and altering the power of the lens assembly. If the lenses are made from a soft material, such as a lens shaped sack filled with polyvinyl alcohol, they also pull into a flatted form enhancing optical power change. To facilitate inserting the lens assembly through an incision, soft lenses could be made of a gel forming polymer and dehydrated (thus shrinking them) and the cell left unfilled until after insertion. After insertion fluids from the surrounding tissue could reconstitute the lenses and fill the cell. The cell could also be filled with a microtube or hypodermic.

Figure 5:
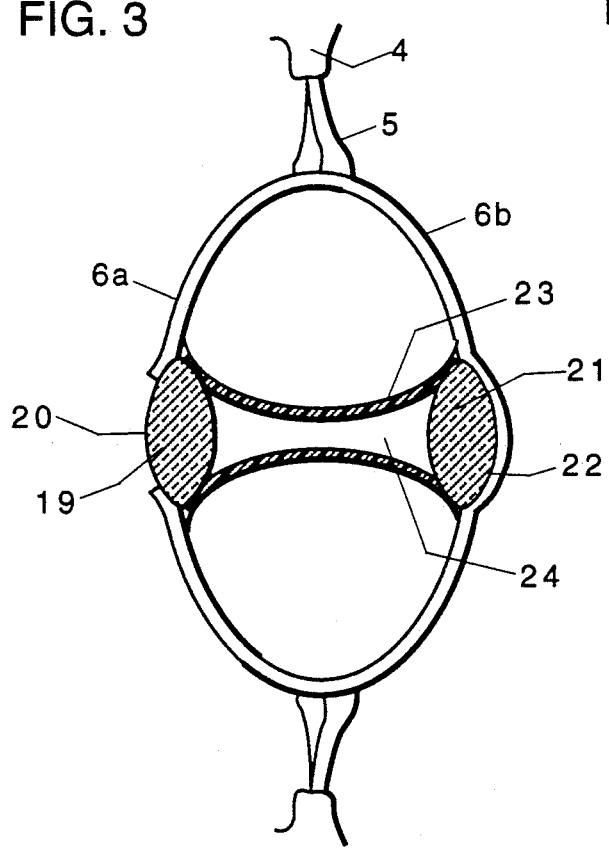
FIG. 5 is a partial sectional view showing an alternate embodiment.
Figure 10:
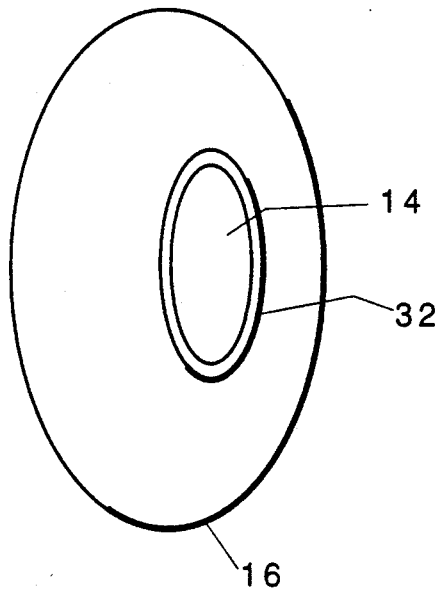
FIG. 10 is a perspective view of a lens assembly having a pliable optic and equatorial support ring.

FIG. 5 shows an alternative form of the invention. In capsular bag 6 is a lens assembly having an anterior lens 19 with anterior curved surface 20 and a posterior lens 21 with posterior curved surface 22. Extending from and connecting the equatorial perimeters of the anterior and posterior lenses is a flexible, resilient cell wall 23 having a diameter substantially the same as lenses 19 and 21. The substantially paraboloid cell 24 thus formed may be filled with a fluid (gas or liquid) such as air. Two or more resilient haptics may be substituted for the cell wall to space the lenses and bias them against the capsular poles. The springlike action of the haptics or cell wall bias the lenses against the surface of the capsular poles supporting the lens assembly in place. As the capsular bag is pulled and released by the ciliary muscles, the lenses approach and withdraw from each other to provide focal accommodation. If a soft lens is used a support ring 32, as shown in FIG. 10, may be provided around the equator of the lens.

Figure 7:
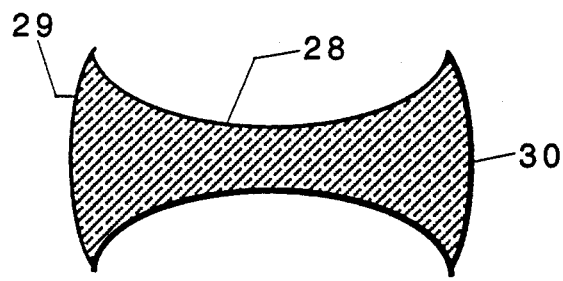
FIG. 7 is a side view of a thick lens embodiment of the lens assembly.

FIG. 7 shows an embodiment of the invention comprising a thick lens having an anterior surface 29 and a posterior surface 30. The body of the lens 28 is substantially paraboloid. Paraboloid for the purposes of this invention includes cylindrical, hyperboloid and paraboloid. The lens is made of a resilient material to bias the anterior and posterior surfaces against the capsular poles. This springlike action supports the lens in place such that when the capsular bag is pulled and released, the anterior and posterior surfaces approach and withdraw from each other providing focal accommodation.

The lens assemblies shown in FIGS. 5 and 7 can be inserted through an incision substantially the width of the lens then turned or be compressed for insertion.

What is claimed is:

1. An accommodative intraocular lens assembly for placement in the capsular bag of the posterior chamber of an eye from which the natural lens has been removed comprising:
   an anterior converging lens having a convex anterior surface and a posterior surface, an equatorial perimeter and an optic axis said anterior lens being at least substantially as large as any permanent opening in the anterior capsule of the eye in which the lens assembly is intended to be inserted;
   a posterior lens having an anterior surface, a posterior surface, an equatorial perimeter and an optic axis substantially parallel to said optic axis of said anterior lens; and
   a wall extending from said equatorial perimeter of said anterior lens to said equatorial perimeter of said posterior lens forming a substantially closed cell for containing a fluid, such that as said capsular bag is pulled and release by ciliary muscles, said lenses approach and withdraw from each other to provide focal accommodation.

2. The lens assembly of claim 1 wherein said posterior lens is a converging lens.

3. The lens assembly of claim 2 wherein said posterior surface of said posterior lens is non-spherically convex.

4. The lens assembly of claim 2 wherein said posterior surface of said posterior lens has a radius of curvature in the range of 4.5 and 7 mm.

5. The lens assembly of claim 2 wherein said anterior surface of said anterior lens has a radius of curvature in the range of 17.7 and 17.9 mm.

6. The lens assembly of claim 2 wherein said posterior surface of said posterior lens has a radius of curvature in the range of 10.6 and 10.8 mm.

7. The lens assembly of claim 1 wherein said cell is substantially paraboloid.

8. The lens assembly of claim 7 wherein said wall is resilient such that said anterior and posterior lenses are biased against said capsular bag when in use.

9. The lens assembly of claim 8 wherein said wall is compressible for insertion into an incision having a length in the range of 2 to 4 mm.

10. The lens assembly of claim 1 wherein said cell is substantially discoid.

11. The lens assembly of claim 10 wherein said cell is substantially ellipsoid.

12. The lens assembly of claim 10 wherein said cell has an equatorial diameter in the range of 9 to 14 mm.

13. The lens assembly of claim 10 wherein said cell has an equatorial diameter in the range of 9 to 10 mm.

14. The lens assembly of claim 10 wherein said wall has a thickness of about 0.1 mm.

15. The lens assembly of claim 10 wherein said closed cell is inflatable.

16. The lens assembly of claim 1 wherein said anterior and posterior lenses have equatorial diameters in the range of 3 to 7 mm.

17. The lens assembly of claim 1 wherein said anterior and posterior lenses have equatorial diameters in the range of 4 to 5 mm.

18. The lens assembly of claim 1 wherein said anterior surface of said anterior lens is non-spherically convex.

19. The lens assembly of claim 1 wherein said anterior lens has a thickness in the range of 1.0 and 1.5 mm.

20. The lens assembly of claim 1 wherein said anterior surface of said anterior lens has a radius of curvature in the range of 8 and 14 mm.

21. The lens assembly of claim 1 wherein at least one of said lenses is rigid.

22. The lens assembly of claim 21 wherein said lenses are made from a polymer chosen from group consisting of methacrylates, polycarbonates, siloxanes and polysulfones.

23. The lens assembly of claim 22 wherein said wall is made from a material chosen from the group consisting of methacrylates and olefins.

24. The lens assembly of claim 1 wherein at least one of said lenses is pliable.

25. The lens assembly of claim 24 wherein said at least one pliable lens is made from a material chosen from the group consisting of gel forming polymers and polyvinyl alcohols.

26. The lens assembly of claim 25 wherein said at least one pliable lens is dehydrated prior to insertion.

27. The lens assembly of claims 24 wherein said at least one pliable lens is provided with an equatorial support ring.

28. The lens assembly of claim 1 wherein the distance between said anterior and posterior lenses is in the range of 3.5 to 5 mm.

29. The lens assembly of claim 1 wherein the distance between the anterior and posterior lenses is about 4 mm.

30. The lens assembly of claim 1 wherein the optical power of said assembly is divided between said anterior and posterior lenses.

31. The lens assembly of claim 1 wherein the power of said assembly is equal to the power of one of said lenses.

32. The lens assembly of claim 1 wherein said wall is made of a material chosen from the group consisting of methacrylates polymers, silicon polymers and olefin polymers.

33. The lens assembly of claim 1 wherein said lens assembly forms a resilient paraboloid.

* * * * *